US006627158B1

(12) United States Patent  
Peltier

(10) Patent No.: US 6,627,158 B1  
(45) Date of Patent: Sep. 30, 2003

(54) DEVICE FOR DEPOSITING CELLS ON AN ANALYTICAL PLATE

(75) Inventor: Eric Peltier, 16 rue des Morteaux, 92160 Antony (FR)

(73) Assignees: Labonord, Templemars (FR); Eric Peltier, Antony (FR)

( * ) Notice: Subject to any disclaimer, the term of this patent is extended or adjusted under 35 U.S.C. 154(b) by 0 days.

(21) Appl. No.: 09/549,712

(22) Filed: Apr. 14, 2000

(30) Foreign Application Priority Data

Apr. 14, 1999 (FR) .............................. 99 04663

(51) Int. Cl.[7] .............................. B01L 3/02; B01L 3/00; B01L 11/00; G01N 21/00; G01N 31/22; G01N 33/48; C12M 1/34; C12M 3/00; C12M 1/12

(52) U.S. Cl. .................. 422/100; 422/99; 422/101; 422/102; 422/58; 436/63; 436/46; 435/287.7; 435/297.5; 435/40.51

(58) Field of Search .................. 422/100, 102, 422/57, 58, 99, 101; 435/40.51, 297.5, 287.7; 436/63, 46

(56) References Cited

U.S. PATENT DOCUMENTS

| 3,690,836 A | * | 9/1972 | Buissiere et al. ............ 422/56 |
| 3,783,105 A | | 1/1974 | Moyer et al. |
| 3,810,739 A | * | 5/1974 | Nussbaum ............... 435/287.7 |
| 4,693,834 A | | 9/1987 | Hossom |
| 4,738,823 A | * | 4/1988 | Engelmann ................. 422/56 |
| 4,895,666 A | | 1/1990 | Franzen et al. |
| 5,081,017 A | | 1/1992 | Longoria |
| 5,346,672 A | * | 9/1994 | Stapleton et al. |
| 5,441,894 A | * | 8/1995 | Coleman et al. |
| 5,503,803 A | * | 4/1996 | Brown |
| 5,593,587 A | | 1/1997 | Fumihiko |
| 5,658,723 A | * | 8/1997 | Oberhardt |
| 5,686,302 A | * | 11/1997 | Zech |
| 5,698,395 A | * | 12/1997 | Ritterband et al. |
| 5,710,049 A | * | 1/1998 | Noppe et al. ............... 436/525 |
| 5,772,961 A | * | 6/1998 | Mico |
| 5,821,073 A | * | 10/1998 | Lee |
| 5,948,695 A | * | 9/1999 | Douglas et al. ............ 436/518 |
| 5,955,352 A | * | 9/1999 | Inoue et al. ............. 435/287.7 |
| 6,162,639 A | * | 12/2000 | Douglass |
| 6,258,327 B1 | * | 7/2001 | Tatum |
| 6,261,523 B1 | * | 7/2001 | Schembri |
| 6,287,783 B1 | * | 9/2001 | Maynard et al. ............ 435/7.1 |
| 6,297,060 B1 | * | 10/2001 | Nowakowski et al. ...... 436/518 |
| 6,350,610 B2 | * | 2/2002 | Egger ..................... 435/287.1 |
| 6,441,898 B1 | * | 8/2002 | Markart ..................... 356/244 |

FOREIGN PATENT DOCUMENTS

| DE | 394 455 | 4/1992 |
| DE | 195 22 246 | 11/1996 |
| EP | 0 334 015 | 9/1989 |
| EP | 0 395 430 | 10/1990 |
| EP | 0 408 225 | 1/1991 |
| GB | 2 291 601 | 1/1996 |

* cited by examiner

*Primary Examiner*—Jill Warden  
*Assistant Examiner*—Brian R Gordon  
(74) *Attorney, Agent, or Firm*—Young & Thompson

(57) ABSTRACT

A device for depositing cells on an analytical plate includes a reception chamber which is to be placed above the analytical plate and whose bottom is open, and a material for absorbing a fixative in a cell suspension in the reception chamber. The absorbent material has a hole therein whose interior wall forms an extension of the reception chamber that defines a gap between the reception chamber and the analytical plate through which the cell fixative is absorbed.

10 Claims, 1 Drawing Sheet

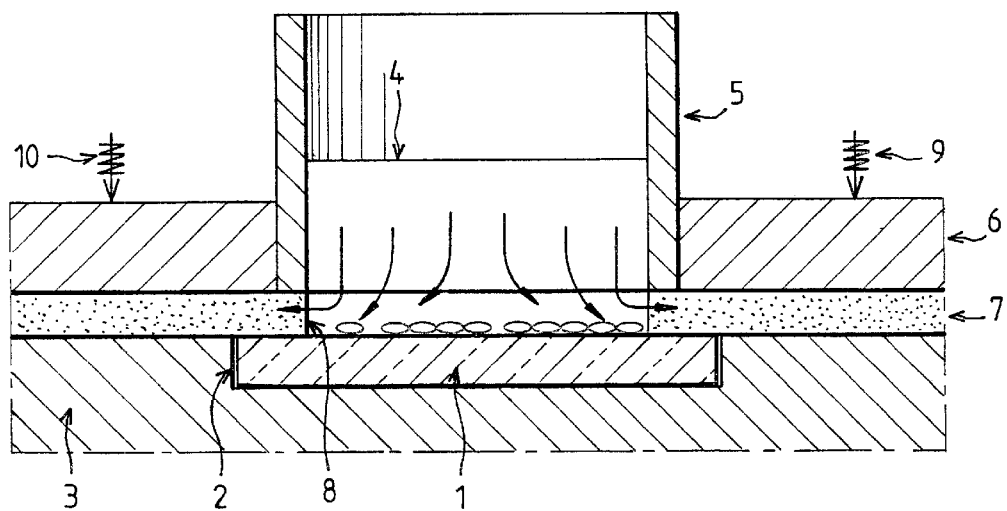

DEVICE FOR DEPOSITING CELLS ON AN ANALYTICAL PLATE

BACKGROUND OF THE INVENTION

The present invention relates to a device for depositing cells on an analytical plate.

In order to detect lesions of the uterine and/or vaginal cervix, cervical or vaginal samples are taken, with these samples making it possible to prepare cyto-logical suspensions with a view to analyzing them.

In a general manner, these samples can be taken using specific brushes which are then introduced into a flask containing a cell fixative so that the sampled cells can be fixed by the fixative and form a suspension with this fixative.

The cells should then be deposited on an analytical plate.

Various procedures and deposition systems for this type of application are already known from the state of the art.

Thus, means for centrifugation and for filtering have, for example, been employed for obtaining this deposition of cells on the plate.

However, such means are relatively complex, cumbersome, expensive and not particularly convenient to use.

The deposition of the cells can also be obtained by simply allowing them to settle.

In this case, the cell suspension, comprising the cell fixative and the cells, is poured into a reception chamber which is placed above the analytical plate and whose bottom is open and extends opposite a cell deposition zone of the analytical plate.

The cells then deposit progressively onto the plate, after which the fixative is removed from the chamber.

However, it can be understood that this settling operation is very lengthy.

SUMMARY OF THE INVENTION

The aim of the invention is therefore to solve these problems.

To this end, the invention relates to a device for depositing cells on an analytical plate, with the said cells being contained in a cell suspension which comprises a cell fixative and the said cells, with the said suspension being poured into a reception chamber which is placed above the analytical plate and whose bottom is open and extends opposite a cell deposition zone of the analytical plate, wherein the bottom of the chamber is in liquid communication with a material for absorbing the fixative for the purpose of absorbing the latter progressively and enabling the cells to be deposited homogeneously on the cell deposition zone of the analytical plate.

BRIEF DESCRIPTION OF THE DRAWINGS

The invention will be more fully understood from reading the description which follows, which is given solely by way of example and which is presented while referring to the attached drawing, which depicts a diagrammatic sectional view of an example of an embodiment of a depositing device according to the invention.

Thus, this FIGURE depicts a device for depositing cells on an analytical plate.

DESCRIPTION OF THE EMBODIMENTS

The analytical plate is designated by the general reference number 1 and is formed by any appropriate plate which is already known in the state of the art.

This plate is accommodated in a corresponding recess 2 of a part 3 which forms a base and which will be described in more detail subsequently.

A cell suspension, designated by the general reference number 4, is poured into a reception chamber 5, which is placed above the analytical plate and whose bottom is open and extends opposite a cell deposition zone of the analytical plate.

This reception chamber 5 is, for example, carried by a support part 6 which will be described in more detail subsequently and which extends opposite the base-forming part 3.

According to the invention, the bottom of the chamber 5 for receiving the cell suspension is located at a distance from the analytical plate 1 and is in liquid communication with a material for absorbing the cell fixative for the purpose of absorbing the latter progressively and enabling the cells to be deposited homogeneously on the cell deposition zone of the plate.

This absorption material is designated in this FIGURE by the general reference number 7 and is present, for example, in the form of a sheet of blotting paper which is provided with a hole 8 which is adjusted to extend opposite the cell deposition zone of the analytical plate.

The absorption material then extends around the cell deposition zone of the plate between the latter and the reception chamber 5, so as to enable the fixative to be absorbed progressively.

This sheet of absorption material 7 is therefore placed between the base-forming part 3 and the support part 6 of the chamber 5 for receiving the suspension.

These parts can be fastened and clamped to each other using fastening and clamping means which are designated in this FIGURE by the general reference numbers 9 and 10 and which comprise any appropriate member, such as screws.

The fastening and clamping of these parts to each other then makes it possible to maintain the sheet of absorption material in position by clamping it between these parts.

It can also be understood that the rate at which the fixative is absorbed by the absorption material depends, for example, inter alia, on the quality of this material and on the constraint which is exerted on it by the part forming the base and the support part, thereby making it possible to optimize the homogeneous deposition of the cells on the analytical plate.

It goes without saying, of course, that it is possible to envisage different embodiments of this device, in particular at the level of bringing the bottom of the chamber for receiving the cell suspension into liquid communication with the absorption material.

Thus, for example, stays which define a predetermined gap between the chamber and the plate and absorption pathways for the fixative can be made as one piece with the wall of this chamber.

It can then be understood that this structure makes it possible to rapidly obtain a homogeneous deposition of the cells, in particular in the form of a monolayer, on the analytical plate, thereby facilitating the subsequent analysis of the cells, and that this structure is particularly well suited for analyzing cervical or vaginal cytological suspensions.

What is claimed is:

1. A device for depositing cells on an analytical plate, the cells being contained in a cell suspension which comprises a cell fixative and the cells, the device comprising:

a reception chamber which is to be placed above an analytical plate and whose bottom is open and extends opposite a cell deposition zone of the analytical plate; and a material for absorbing the fixative for the purpose of absorbing the fixative progressively and enabling the cells to be deposited homogeneously on the cell deposition zone of the analytical plate, an interior wall of the material for absorbing the fixative being arranged around the cell deposition zone of the analytical plate, the bottom of the chamber being in liquid communication with the material, wherein the bottom of the reception chamber is separated from the analytical plate by the interior wall of the material when the device is placed on the plate in order to define, between the bottom and the analytical plate, a pathway of liquid communication between the chamber and the material for absorbing the fixative, and wherein the material for absorbing the fixative is maintained in position by being clamped between two parts which are combined with means for fastening and clamping to each other, one of said two parts carries the chamber while the other of said two parts contains a recess below the bottom of the chamber for accommodating the analytical plate.

2. The device as claimed in claim 1, wherein the material for absorbing the fixative is present in the form of a sheet which is provided with a hole whose periphery is the interior wall.

3. The device as claimed in claim 1, wherein the cell suspension is a cervical cytological suspension.

4. The device as claimed in claim 1, wherein the cell suspension is a vaginal cytological suspension.

5. The device as claimed in claim 1, wherein the absorption material is a sheet of blotting paper.

6. A device for depositing cells on an analytical plate, the device comprising:

a reception chamber having an open bottom, said reception chamber for receiving a cell suspension that includes cells in a cell fixative;

an absorbent material that is adapted to absorb a cell fixative in a cell suspension in said reception chamber, said absorbent material having an opening therein that is in registration with said open bottom, said opening having an interior wall that is an axial extension of said reception chamber at said open bottom, said interior wall of said opening being adapted to surround a cell deposition zone on an analytical plate so as to define an open space for depositing cells on the cell deposition zone and a gap between the analytical plate and said reception chamber for passage of the cell fixative into said absorbent material when said device is positioned on the analytical plate; and two plates that sandwich said absorbent material, one of said two plates having a recess below said open bottom for receiving an analytical plate and the other of said two plates carrying said reception chamber.

7. The device of claim 6, wherein said open bottom and said opening having the same diameter.

8. The device of claim 2, wherein said bottom and said hole having the same diameter.

9. A device for depositing cells, the device comprising:

an analytical plate having a cell deposition zone on which cells are deposited;

a reception chamber having an open bottom that is in registration with said deposition zone, said reception chamber receiving a cell suspension that includes cells in a cell fixative;

an absorbent material that is adapted to absorb a cell fixative in a cell suspension in said reception chamber, said absorbent material having an opening therein that is in registration with said open bottom, said opening having an interior wall that is an axial extension of said reception chamber at said open bottom, said interior wall of said opening surrounding said deposition zone so as to define an open space for depositing cells on said deposition zone and a gap between said analytical plate and said reception chamber for passage of the cell fixative into said absorbent material; and two plates that sandwich said absorbent material, one of said two plates having a recess below said open bottom for receiving said analytical plate and the other of said two plates carrying said reception chamber.

10. The device of claim 9, wherein said open bottom and said opening having the same diameter.

* * * * *